United States Patent [19]

Elton et al.

[11] 4,420,471
[45] Dec. 13, 1983

[54] CITRUS FLAVORED MOUTHWASH FORMULATION METHOD

[75] Inventors: Craig T. Elton, Rochelle Park, N.J.; Stephen Reynolds, Maybrook, N.Y.

[73] Assignee: Lever Brothers Company, New York, N.Y.

[21] Appl. No.: 457,093

[22] Filed: Jan. 10, 1983

[51] Int. Cl.³ .......................... A61K 7/16; A61K 7/26
[52] U.S. Cl. ........................................ 424/49; 424/58; 426/651
[58] Field of Search ................................... 424/49–58; 426/651

[56] References Cited

U.S. PATENT DOCUMENTS

| | | | |
|---|---|---|---|
| 2,422,145 | 6/1947 | Taylor | 426/651 |
| 2,435,744 | 2/1948 | Hartman | 426/651 |
| 2,508,978 | 5/1950 | Tribble | 426/651 |
| 3,342,687 | 9/1967 | Gould | 424/49 |
| 3,639,563 | 2/1972 | Januszewski | 424/49 |
| 3,666,476 | 5/1972 | Honey et al. | 426/651 |
| 3,674,502 | 7/1972 | Honey et al. | 426/651 |
| 3,864,472 | 2/1975 | Pensak et al. | 424/54 |
| 3,876,759 | 4/1975 | Pensak et al. | 424/49 |
| 3,947,570 | 3/1976 | Pensak et al. | 424/49 |
| 4,130,638 | 12/1978 | Dhabhar et al. | 424/49 |
| 4,150,151 | 4/1979 | Pader et al. | 424/49 |

OTHER PUBLICATIONS

Walford, J. Food Manuf. 51(2): 35–37(1976) "Solubilizers for Essential Oils in Flavor Formulations".
Schmolka, American Perfumer & Cosmetics 82: 25–30 Jul. 1967, "Applications of Pluronic Polyols in the Cosmetic Industry".

*Primary Examiner*—Shep K. Rose
*Attorney, Agent, or Firm*—Milton L. Honig; James J. Farrell

[57] ABSTRACT

A method is disclosed for preparing visually clear, stable aqueous citrus flavored mouthwash compositions. The procedure reduces flammability hazards associated with mixing volatile alcohols and eliminates the necessity of certain production equipment.

The method for formulating the liquid mouthwash comprises from about 0.01% to about 0.5% of citrus flavor oil, about 0.1% to about 2.0% emulsifier, about 1% to about 25% $C_{2-3}$ alcohol and about 60% to about 95% water, wherein the steps include:

(a) preparing a blend of the alcohol with the citrus flavor oil;
(b) preparing a second blend of water and the emulsifier;
(c) subsequently combining blends (a) and (b); and
(d) intimately mixing the resultant combination.

12 Claims, No Drawings

CITRUS FLAVORED MOUTHWASH FORMULATION METHOD

BACKGROUND OF THE INVENTION

1. Field of the Invention

This invention relates to a method for preparing visually clear, stable aqueous citrus flavored mouthwash compositions in a procedure which reduces flammability hazards associated with mixing volatile alcohols and eliminates the necessity of certain equipment.

2. The Prior Art

Consumers desire pleasant tasting mouthwash. Mint, fruit or spice-type flavors are readily solubilized into mouthwash formulations. A wide spectrum of emulsifiers are available for obtaining stable clear emulsions with these types of flavors. Citrus flavors, however, have proven difficult to formulate with mouthwashes. Insolubility and/or emulsion instability are frequently encountered.

When citrus oil flavors are used in mouthwashes, the compositions frequently become cloudy. Also, a settling-out of certain components during storage often occurs. These undesirable properties have been ascribed to the presence of non-polar terpene components in citrus oil.

Only a limited number of emulsufiers are known that readily solubilize sufficient amounts of citrus oils to yield end products with recognizable citrus flavor. A further restriction is the requirement that only food grade additive emulsifiers be employed. Safe additives are required in view of the possibility of accidental ingestion.

Conventionally, mouthwash products are formulated by mixing emulsifiers, flavor materials and other alcohol-soluble components with alcohol in a suitable mixing apparatus. Water and water-soluble components are then added to the mixing apparatus containing the alcohol solution. The entire contents are then blended to form the final mouthwash product. U.S. Pat. No. 3,639,563 is a typical disclosure of the conventional method.

A method for specifically preparing clear lemon-flavored mouthwash is described in U.S. Pat. No. 3,876,759. Therein, a premix of lemon oil, emulsifier and alcohol are first formed. Subsequently, the alcoholic emulsified lemon oil premix is added to a water solution held in a second mixing tank. Clear stable liquid products are claimed to result from this process.

The aforementioned patents have instructed on the necessity of delivering emulsified flavor first into an alcohol vehicle prior to mixing with water. The flammability hazard associated with separately mixing alcohol and emulsifier can be eliminated with the present invention. Blending equipment need therefore not be fitted with expensive explosion proof electrical motors and other similar safety apparatus. Furthermore, premix equipment also becomes unnecessary where ethanol and emulsifier no longer need be blended together.

Besides clarity and stability, emulsifiers must have acceptable taste properties. Nonionic emulsifiers are known for imparting flavor notes (bitter or sour overtones) to mouthwashes. Flavor oils are not always successful at masking those notes, especially in blends containing modest amounts of flavor oil.

U.S. Pat. No. 3,639,563 provides a solution to the taste problem. Small amounts of chloroform are added to alcohol-nonionic emulsifier containing aqueous mouthwash. Superior taste characteristics are imparted. Unfortunately, chloroform is a suspected carcinogen. Its use in oral applications has been thereby circumscribed.

It is an object of the present invention to disclose a method for preparing clear, stable citrus flavored mouthwash products.

Another object of this invention is to obtain a clear, stable citrus flavored mouthwash by a method that minimizes the flammability hazard of handling ethanol and that reduces capital costs by requiring fewer mixing vessels.

It is a further object of this invention to identify emulsifiers that can be effectively used in the method of the present invention.

Furthermore, it is an object of the present invention to prepare citrus flavored mouthwash by an improved method comprising an emulsifier that provides not only clear, stable formulations but that also does not impart the bad flavor notes of the emulsifier.

SUMMARY OF THE INVENTION

A method of formulating a liquid mouthwash is disclosed comprising from about 0.01 to about 0.5% citrus flavor oil, about 0.1 to about 2.0% emulsifier, about 1 to about 25% $C_{2-3}$ alcohol and about 60 to about 95% water, including the steps of:

(a) preparing a blend of the alcohol with the citrus flavor oil;
(b) preparing a second blend of water and the emulsifier;
(c) subsequently combining blends (a) and (b); and
(d) intimately mixing the resultant combination.

DETAILED DESCRIPTION OF THE INVENTION

A stable, clear citrus flavored mouthwash is prepared by mixing ethanol with citrus flavor. This mixture is then added to a water solution containing a food additive approved low-off flavor nonionic emulsifier, a humectant and dyes. Additional ingredients such as sodium lauryl sulfate, saccharin and other typical mouthwash components may be either dissolved prior to or subsequent to the addition of the ethanol/flavor mix.

The subject process allows for the mixing of all normally used mouthwash ingredients with the exception of the flavor and ethanol into the water phase of the formulation. Dependant upon the exact formulation of the mouthwash and the mixing facilities, the order of ingredient addition can be varied. The only restriction is that the emulsifier be mixed into the water prior to the addition of the ethanol/flavor blend.

Among the citrus flavor oils that may be employed are lemon, grapefruit, orange, mandarin orange, lime, Mexican lime, tangarine and tangello oils and mixtures thereof. Natural or synthetic citrus flavor oils or mixtures thereof are suitable for use in the present invention. Lemon Oil 360, manufactured by Glidden-Durkee Corp., exemplifies a lemon flavor of the synthetic variety suitable for use herein. C&A Lemon Oil, manufactured by the Citrus & Allied Company, is exemplative of a natural lemon oil useful within the instantly described mouthwashes. Citrus flavor oils can be employed in an amount from about 0.01 to about 0.5%. Preferably, a concentration range of from about 0.1 to about 0.25% is employed.

According to the instant process, a clear, stable citrus flavored mouthwash can be formulated with the use of certain polymeric polyoxyethylene-containing nonionic emulsifiers.

Among the nonionic emulsifiers that can be employed within the present invention are:

(i) polyoxyethylene derivatives of sorbitan mono-, di-, and tri-fatty acid esters wherein the fatty acid component has between 12 and 24 carbon atoms. The preferred polyoxyethylene derivatives are of sorbitan monolaurate, sorbitan trilaurate, sorbitan monopalmitate, sorbitan tripalmitate, sorbitan monostearate, sorbitan monoisostearate, sorbitan tristearate, sorbitan monooleate and sorbitan trioleate. The polyoxyethylene chains may contain between about 4 and 30 ethylene oxide units, preferably about 20. The sorbitan ester derivatives contain 1, 2 or 3 polyoxyethylene chains dependent upon whether they are mono-, di- or tri-acid esters.

Especially preferred commercial embodiments of this type of emulsifier are Polyoxyethylene 20 Sorbitan Trioleate, Polyoxyethylene 20 Sorbitan Monooleate, Polyoxyethylene 20 Sorbitan Tristearate, Polyoxyethylene 20 Sorbitan Monostearate, Polyoxyethylene 20 Sorbitan Monopalmitate and Polyoxyethylene 20 Sorbitan Monolaurate. These surfactants are available from ICI Americas, Inc., under the trademark "Tween 85," "Tween 80, " "Tween 65, " "Tween 60," "Tween 40" and "Tween 20," respectively. The most preferred example of these emulsifiers is Polyoxyethylene 20 Sorbitan Monopalmitate because of its innocuous taste property.

(ii) Polyoxyethylene derivatives of fatty alcohols wherein the fatty alcohol component has between 12 and 24 carbon atoms. The polyoxyethylene chains may contain between about 4 and 30 ethylene oxide units, preferably about 20. A preferred emulsifier within this group is Polyoxyethylene 20 Isohexadecyl Ether. Commercially, this polyether is available under the trademark "Arlasolve 200," sold by ICI Americas, Inc. "Arlasolve 200" displayed excellent taste properties even where only low levels (0.10%) citrus flavor oils were present.

(iii) Polyoxyethylene derivatives of fatty acids wherein the fatty acid component has between 12 and 24 carbon atoms. The polyoxyethylene chains may contain between about 4 and 50 ethylene oxide units, preferably about 40. A preferred example of this type of emulsifier is Polyoxyethylene 40 Stearate, commerically available under the trademark "Myrj 52," manufactured by ICI Americas, Inc. Not only were clear, stable mouthwashes achievable with "Myrj 52" but they also were of acceptable taste.

Other emulsifiers within this category capable of delivering clear, stable solutions with the herein disclosed process include: Polyoxyethylene 10 Oleyl Ether, Polyoxyethylene 20 Oleyl Ether and Polyoxyethylene 20 Stearyl Ether. These compounds are sold by ICI Americas, Inc., under the trademarks of "Brij 96," "Brij 99" and "Brij 78," respectively,. Unlike the aforementioned "Myrj," "Arlasolve" and "Tween" compounds, mouthwashes containing the "Brij" materials did not have the fine taste properties when formulated with only small amounts of citrus flavor oils.

Polyoxyethylene-polyoxypropylene stearate, commercially available as "Atlas G-2162" from ICI Americas, Inc., also afforded clear, stable mouthwash solutions using the herein disclosed method of preparation. However, mouthwashes containing "Atlas G-2162" had poor taste characteristics when formulated with only small amounts of citrus flavor oils. Higher citrus flavor levels were operative in masking the taste of "Atlas G-2162" but clear products were not obtained.

Polyoxyethylene-polyoxypropylene block polymers do not afford clear solutions with the citrus flavor oil formulations of this invention. These polymers are condensates of ethylene oxide with a hydrophobic base formed by condensing propylene oxide with propylene glycol. Commercial examples of this type emulsifier are the "Pluronics," a trademark of BASF-Wyandotte Corporation.

The surfactant emulsifier of this invention should be present in an adequate amount to completely emulsify the citrus flavoring ingredient to produce a clear, stable product. Typically, the emulsifier is present from about 0.1 to about 2% of the formulation depending on the alcohol and citrus oil concentration. Preferably, the emulsifier concentration should be present from about 0.25 to about 0.75%. Within the aforementioned ranges, the amount of surfactant should be proportional to the amount of citrus flavor oil; the greater the amount of oil, the greater the amount of surfactant.

Mouthwash compositions according to the present invention typically contain from about 60 to about 95% water. More preferably, the formulation contains from about 75 to about 85% water.

A non-toxic alcohol such as ethanol, isopropanol or mixtures thereof is also present within the mouthwash formulation. Their concentration is typically from about 1 to about 25%, preferably from about 10 to about 20%. All percentages described herein are by weight of the total mouthwash composition.

Nonionic emulsifiers other than those described above may not function at reasonable levels (below 0.75%) to yield a clear, stable end product. Many of those emulsifiers that meet this requirement may nevertheless have such an "off" flavor as to render the end product non-acceptable. Food additive approved emulsifiers must be present in at least 0.1% to solubilize the flavor oils and concomitantly yield an acceptable/recognizable citrus flavored product. At 0.75% and above, most emulsifiers possess an inherent bitter flavor which is not readily masked by citrus flavor oils.

The water phase, either prior to or after the addition of alcohol/flavor oil may contain adjunct mouthwash ingredients. There may be present humectants (some of which may also function as sweeteners) such as corn syrup, corn syrup derivatives, glycerine, sorbitol, sorbitol derivatives or propylene glycol or mixtures thereof. Non-crystallizable sorbitols such as "Polyol A-641" and "Polyol A-625" are examples of commercial humectants/sweeteners suitable for use with mouthwashes of this invention. These materials are manufactured by ICI Americas, Inc. Also present may be synthetic or natural sweeteners, colorants and therapeutic materials for the improvement of oral health, anti-cavity or anti-bacterial activity. Suitable sweetening agents include sucrose, lactose, maltose, sorbitol, sodium cyclamate, xylitol, saccharin and aspartame (a product of Searle & Co.).

Flavor adjunct materials to accentuate tartness may be added to the water phase at any point in the process. These tartness accentuators are water-soluble $C_2$–$C_{10}$ monocarboxylic or dicarboxylic acids or their alkali or alkaline earth metal salts. Preferred examples of these accentuators are citric, ascorbic, acetic, malic, succinic, fumaric and maleic acids or acid salts and mixtures thereof.

Electrolytes and anionic surfactants may also be added to the water phase at any point in the process. Examples of suitable electrolytes include the water-soluble alkali and alkaline earth metal chlorides, bromides, fluorides, sulfates and phosphates. Particularly preferred is sodium chloride. Among the anionic surfactants, alkyl sulfates, aryl and alkyl sulfonates and alkylaryl sulfonates are preferred. Especially effective is sodium lauryl sulfate.

The method of this invention can be conducted at atmospheric pressure. Temperatures can range from about 50° to 110° F.; preferably from about 70° to 100° F. These temperatures allow for rapid dissolution of the ingredients while not allowing for excessive vaproization of alcohol.

The following examples will more fully illustrate the embodiments of this invention. All parts, percentages and proportions referred to herein and in the appended claims are by weight unless otherwise illustrated.

EXAMPLES 1-38

Typical of the mouthwash formulations encompassed by this invention is the following composition:

| Ingredient | % by Weight |
|---|---|
| 190 Proof ethanol | 12.5 |
| Flavor oil | 0.01-0.5 |
| Nonionic emulsifier | 0.1-2.0 |
| Glycerine | 4.50 |
| Sodium Lauryl Sulfate | 0.30 |
| Sodium saccharin | 0.06 |
| Sodium chloride | 0.05 |
| Sodium citrate | 0.03 |
| 1% Yellow 10 Dye Solution | 0.50 |
| Distilled water | until 100% |
| Total | 100.00 |

Ethanol and the citrus flavor oil were first combined. Thereafter, the ethanolic citrus flavor oil solution was added to a vessel containing the nonionic emulsifier ("Tween 80"), glycerine, sodium lauryl sulfate, saccharin, sodium chloride, sodium citrate and dye in aqueous solution. A stirrer continuously mixed the aqueous phase during the approximately 15 minute ethanol/citrus oil addition period. Stirring was continued for approximately another 15 minutes thereafter. A blend temperature of 70°-100° F. was maintained throughout.

Using the above general formula and procedure, 38 mouthwashes were prepared each containing various concentrations of "Tween 80" and different citrus flavor oils. These blends are listed in Table I wherein the specific concentrations of "Tween 80" and citrus oil are delineated. Solution clarities were determined by means of the Nessler tube clarity test, described hereafter.

The Nessler tube, a glass tube of 14¾ inches long with a diameter of approximately ⅞ of an inch is made of clear glass. One end is open while the other closed in a flat bottom configuration. Two distinctly printed markings are found on the tube—50 ml and 100 ml. The markings indicate the quantity of substance in the tube. To limit spillage, there is approximately 3½ inches of excess space on the top of the 100 ml reading.

The procedure for taking a clarity reading using the tube for mouthwash is as follows:

1. A clean tube is filled to the 100 ml level. The tube is kept standing until all air bubbles and foam (if any) have dissipated.
2. The test tube is stood upright on top of a RIT Alphanumeric resolution test object sheet RT-4-74.

A RIT sheet is a chart approximately 8½" by 8½" which contains a series of characters in sets of 3 which lie next to an integer (+). The more positive the integer, the smaller the set of characters.

3. The smallest set of characters the observer can see clearly is noted and recorded.

TABLE I

CLARITY OF CITRUS FLAVOR MOUTHWASHES CONTAINING TWEEN 80

| Example | Tween 80 Emulsifier (conc., %) | Flavor Oil | Flavor Oil (conc., %) | Observation | Nessler Tube Reading |
|---|---|---|---|---|---|
| 1 | 0.50 | Glidden 360 Lemon Oil | 0.10 | Very clear | +13 |
| 2 | 0.50 | Glidden 360 Lemon Oil | 0.15 | Clear | +12 |
| 3 | 0.50 | Glidden 360 Lemon Oil | 0.13 | Clear | +12 |
| 4 | 1.00 | Glidden 360 Lemon Oil | 0.20 | Clear | +13 |
| 5 | 1.00 | Glidden 360 Lemon Oil | 0.23 | Clear | +13 |
| 6 | 1.00 | Glidden 360 Lemon Oil | 0.27 | Clear | +12 |
| 7 | 0.50 | Grapefruit | 0.10 | Clear | +12 |
| 8 | 1.00 | Grapefruit | 0.25 | Not clear | −12 |
| 9 | 1.00 | Grapefruit | 0.20 | Not clear | −1 |
| 10 | 1.00 | Grapefruit | 0.18 | Almost clear | +5 |
| 11 | 1.00 | Grapefruit | 0.16 | Clear | +7 |
| 12 | 1.00 | Grapefruit | 0.10 | Clear | +11 |
| 13 | 0.50 | Mandarin Oil | 0.13 | Clear | +13 |
| 14 | 0.50 | Mandarin Oil | 0.15 | Clear | +12 |
| 15 | 1.00 | Mandarin Oil | 0.25 | Not clear | −3 |
| 16 | 1.00 | Mandarin Oil | 0.20 | Clear | +12 |
| 17 | 1.00 | Mandarin Oil | 0.22 | Not clear | −4 |
| 18 | 0.50 | C + A Lemon Oil | 0.10 | Clear | +13 |
| 19 | 0.50 | C + A Lemon Oil | 0.15 | Clear, slight cloud forming | +12 |
| 20 | 0.50 | C + A Lemon Oil | 0.13 | Clear | +13 |
| 21 | 1.00 | C + A Lemon Oil | 0.20 | Extremely clear | +13 |
| 22 | 1.00 | C + A Lemon Oil | 0.25 | Almost clear starting cloud | +13 |
| 23 | 0.50 | Mexican Lime Oil | 0.10 | Clear | +13 |
| 24 | 0.50 | Mexican Lime Oil | 0.13 | Clear | +13 |
| 25 | 0.50 | Mexican Lime Oil | 0.15 | Clear | +13 |
| 26 | 0.50 | Mexican Lime Oil | 0.18 | Clear | +12 |
| 27 | 1.00 | Mexican Lime Oil | 0.18 | Clear | +13 |
| 28 | 1.00 | Mexican Lime Oil | 0.25 | Clear | +13 |
| 29 | 1.00 | Mexican Lime Oil | 0.30 | Clear | +13 |
| 30 | 0.50 | Tangerine Oil Florida | 0.10 | Borderline clear | +10 |
| 31 | 1.00 | Tangerine Oil Florida | 0.17 | Clear | +10 |

TABLE I-continued

CLARITY OF CITRUS FLAVOR MOUTHWASHES CONTAINING TWEEN 80

| Example | Tween 80 Emulsifier (conc., %) | Flavor Oil | Flavor Oil (conc., %) | Observation | Nessler Tube Reading |
|---|---|---|---|---|---|
| 32 | 1.00 | Tangerine Oil Florida | 0.20 | Clear | +13 |
| 33 | 1.00 | Tangerine Oil Florida | 0.23 | Cloudy | +11 |
| 34 | 0.25 | Glidden 360 Lemon Oil | 0.10 | Clear | +12 |
| 35 | 0.25 | C + A Lemon Oil | 0.10 | Not clear | −3 |
| 36 | 0.25 | Mandarin Oil | 0.10 | Clear | +12 |
| 37 | 0.25 | Mexican Lime Oil | 0.10 | Clear | +12 |
| 38 | 0.25 | Grapefruit Oil | 0.10 | Not clear | −12 |

EXAMPLES 39–44

Mouthwash compositions were blended according to the basic formulation and procedure of Examples 1–38. Only the emulsifier, the flavor oil and their concentrations were varied. These parameters are listed in Table II.

To achieve clear solutions at citrus flavor oil levels of 0.25%, the "Brij" and "Tween" brand emulsifiers, with but one exception, were required in concentrations above 0.40 or 0.50%. Table II illustrates this fact.

TABLE II

CLARITY EVALUATION OF VARIOUS EMULSIFIERS AND FLAVOR OILS

| Example | Emulsifier | Flavor Oil | Oil Level | Clarity |
|---|---|---|---|---|
| 39 | TWEEN 40 0.40% | Glidden 360 C & A Lemon Grapefruit Mandarin | .25% | Not clear |
| 40 | BRIJ 98 0.50% | Glidden 360 C & A Lemon Grapefruit Mandarin | .25% | Not clear |
| 41 | BRIJ 96 0.50% | Glidden 360 C & A Lemon Grapefruit Mandarin | .25% .25% | +10 clear Not clear |
| 42 | BRIJ 99 0.50% | Glidden C & A Lemon Grapefruit Mandarin | .25% | Not clear |
| 43 | BRIJ 78 0.50% | Glidden 360 C & A Lemon Grapefruit Mandarin | .25% | Not clear |
| 44 | ATLAS G 2162 0.50% | Glidden 360 C & A Lemon Grapefruit Mandarin | .25% | Not clear |

EXAMPLES 45–50

Examples 45–50 represent mouthwashes comprised of the components outlined in the general formula and prepared by the method of Example 1–38. Specific emulsifiers, flavor oils and their concentrations are itemized in Table III.

Citrus flavor oil levels as low as 0.01% (of total product) still afforded identifiable fruit flavor.

Clear, stable solutions were obtained for 0.10% citrus flavor containing blends employing 0.75% of "Tween 40," "Brij 96," "Brij 78," "Brij 98" and "Brij 99." "Atlas G 2162" did not afford perfectly clear solutions with all types of citrus oils. Only with Glidden 360 Lemon Oil and with Lime Oil, did Atlas G 2162 achieve good clarity.

Only the "Tween 40" formulation afforded an acceptable tasting mouthwash at concentration levels described by Table III. None of the other five emulsifiers gave acceptably tasting mouthwashes.

TABLE III

CLARITY AND FLAVOR EVALUATION OF VARIOUS EMULSIFIERS AND FLAVOR OILS

| Example | Emulsifier | Flavor Oil | Oil Level | Clarity | Flavor |
|---|---|---|---|---|---|
| 45 | TWEEN 40 0.75% | Glidden 360 | .10% | +13 clear | Acceptable |
| | | C & A Lemon | .10% | +13 clear | " |
| | | Grapefruit | .10% | +12 clear | " |
| | | Mandarin | .10% | +13 clear | " |
| | | Lime | .10% | +13 clear | " |
| 46 | BRIJ 96 0.75% | Glidden 360 | .10% | +13 clear | Poor |
| | | C & A Lemon | .10% | +13 clear | " |
| | | Grapefruit | .10% | +13 clear | " |
| | | Mandarin | .10% | +13 clear | " |
| | | Lime | .10% | +13 clear | " |
| 47 | BRIJ 78 0.75% | Glidden 360 | .10% | +12 clear | Poor |
| | | C & A Lemon | .10% | +13 clear | " |
| | | Grapefruit | .10% | +13 clear | " |
| | | Mandarin | .10% | +12 clear | " |
| | | Lime | .10% | +12 clear | " |
| 48 | BRIJ 98 0.75% | Glidden 360 | .10% | +13 clear | Poor |
| | | C & A Lemon | .10% | +13 clear | " |
| | | Grapefruit | .10% | +12 clear | " |
| | | Mandarin | .10% | +12 clear | " |
| | | Lime | .10% | +12 clear | " |
| 49 | BRIJ 99 0.75% | Glidden 360 | .10% | +13 clear | Poor |
| | | C & A Lemon | .10% | +13 clear | " |
| | | Grapefruit | .10% | +12 clear | " |
| | | Mandarin | .10% | +13 clear | " |
| | | Lime | .10% | +13 clear | " |
| 50 | ATLAS G 2162 | Glidden 360 | .10% | +13 clear | Poor |

TABLE III-continued

CLARITY AND FLAVOR EVALUATION OF VARIOUS EMULSIFIERS AND FLAVOR OILS

| Example | Emulsifier | Flavor Oil | Oil Level | Clarity | Flavor |
|---|---|---|---|---|---|
| | 0.75% | C & A Lemon | .10% | +10 cloudy | " |
| | | Grapefruit | .10% | +8 | " |
| | | Mandarin | .10% | +5 | " |
| | | Lime | .10% | +12 clear | " |

EXAMPLE 51

To evaluate the applicability of employing polyoxypropylene-polyoxyethylene block polymers as used in U.S. Pat. Nos. 3,876,759 and 3,639,563 in the process of the present invention, a series of mouthwash formulations were prepared containing Pluronic F-108. Pluronic F-108 is a typical polyoxypropylene-polyoxyethylene block polymer of molecular weight 16,000 sold by BASF-Wyandotte Corporation. The ingredients of these mouthwashes are listed below. They were prepared by combining citrus flavor oil with ethanol and then adding the alcoholic solution to the aqueous phase. Besides water, the latter contained Pluronic F-108, sodium lauryl sulfate, saccharin, sodium chloride, acetate buffer, Polyol A-625 and dye. Polyol A-625 is a noncrystallizable sorbitol sold by ICI Americas, Inc. Mixing conditions were essentially identical to those disclosed in Examples 1-38.

| Ingredient | % by Weight |
|---|---|
| 190 Proof Ethanol | 12.5 |
| Flavor Oil | 0.1 |
| Pluronic F-108 | 0.75 |
| Sodium Lauryl Sulfate | 0.30 |
| Sodium Saccharin | 0.065 |
| Sodium Chloride | 0.03 |
| Acetate Buffer | 0.50 |
| Polyol A-625 | 7.0 |
| 1% Yellow 10 Dye Solution | 0.025 |
| Distilled Water | until 100% |
| Total | 100.00 |

Four separate blends were evaluated for clarity using different citrus flavor oils. The flavor oils employed were Mandarin Oil Italian (Citrus & Allied Co.), Lime Oil Florida (Polarome Corp.), Lemon Oil 360 (Glidden-Durkee Corp.) and Lemon Oil California (Citrus & Allied Co.).

All the flavor oils afforded only cloudy solutions. None were visually clear. Accordingly, Pluronic F-108 and similar structured emulsifiers would not provide the clear solutions contemplated within the present invention.

The foregoing description and examples illustrate selected embodiments of the present invention and in light thereof various modifications will be suggested to one skilled in the art, all of which are within the spirit and purview of this invention.

What is claimed is:

1. A method of formulating a liquid mouthwash comprising from about 0.01 to about 0.5% of citrus flavor oil, about 0.1 to about 2.0% emulsifier, about 1% to about 25% $C_{2-3}$ alcohol and about 60 to about 95% part water, including the steps of:
   (a) preparing a blend of the alcohol with the citrus flavor oil;
   (b) preparing a second blend of water and the emulsifier;
   (c) subsequently combining blends (a) and (b); and
   (d) intimately mixing the resultant combination.

2. A method according to claim 1 wherein the alcohol is ethanol or isopropanol or mixtures thereof.

3. A method according to claim 1 wherein the emulsifier is a polymeric polyoxyethylene-containing nonionic surfactant chosen from the group consisting of Polyoxyethylene 20 Isohexadecylether, Polyoxyethylene 20 Sorbitan Trioleate, Polyoxyethylene 20 Sorbitan Monooleate, Polyoxyethylene 20 Sorbitan Tristearate, Polyoxyethylene 20 Sorbitan Monostearate, Polyoxyethylene 20 Sorbitan Monopalmitate and Polyoxyethylene 20 Sorbitan Monolaurate and mixtures thereof.

4. A method according to claim 1 wherein the citrus flavor oil is chosen from the group consisting of lemon, grapefruit, orange, mandarin orange, tangarine, tangello, Mexican lime and lime and mixtures thereof.

5. A method according to claim 1 wherein the citrus flavor oil is of synthetic or natural origin.

6. A method according to claim 1 wherein the emulsifier is present from about 0.25 to about 0.75%.

7. A method according to claim 1 wherein the citrus flavor oil is present from about 0.1 to about 0.25%.

8. A method according to claim 1 wherein the alcohol is present from about 10 to about 20%.

9. A method according to claim 1 wherein water is present from about 75 to about 85%.

10. A method according to claim 1 wherein adjunct mouthwash ingredients are added to the water phase prior to or after the addition of alcohol flavor oil, said ingredients selected from the group consisting of humectants, sweeteners, colorants, flavor adjuncts, oral health therapeutic agents, anti-bacterials, anti-cavity agents and electrolytes and mixtures thereof.

11. A method according to claim 10 wherein the flavor adjunct ingredient is a water-soluble $C_2-C_{10}$ monocarboxylic or dicarboxylic acid or its alkali or alkaline earth metal salt.

12. A method according to claim 11 wherein the flavor adjunct acid or acid salt is selected from the group consisting of citric, ascorbic, acetic, malic, succinic, fumaric and maleic acids or acid salts and mixtures thereof.

* * * * *